(12) United States Patent (10) Patent No.: US 7,717,960 B2
Schneier (45) Date of Patent: May 18, 2010

(54) DYNAMIC SPINAL IMPLANT OR JOINT REPLACEMENT

(76) Inventor: Michael Schneier, 2114 N. Crescent Blvd., Yardley, PA (US) 19067-3056

( * ) Notice: Subject to any disclaimer, the term of this patent is extended or adjusted under 35 U.S.C. 154(b) by 0 days.

(21) Appl. No.: 11/254,615

(22) Filed: Oct. 20, 2005

(65) Prior Publication Data

US 2006/0089720 A1 Apr. 27, 2006

Related U.S. Application Data

(60) Provisional application No. 60/621,118, filed on Oct. 22, 2004.

(51) Int. Cl.
*A61F 2/44* (2006.01)
(52) U.S. Cl. ............... 623/17.15; 623/17.14; 623/17.16
(58) Field of Classification Search .............. 623/17.16, 623/17.14, 17.11
See application file for complete search history.

(56) References Cited

U.S. PATENT DOCUMENTS

| | | | | |
|---|---|---|---|---|
| 5,314,477 A | * | 5/1994 | Marnay | 623/17.15 |
| 5,893,889 A | * | 4/1999 | Harrington | 623/17.16 |
| 5,899,941 A | * | 5/1999 | Nishijima et al. | 623/17.15 |
| 6,440,168 B1 | * | 8/2002 | Cauthen | 623/17.14 |
| 6,579,321 B1 | * | 6/2003 | Gordon et al. | 623/17.16 |
| 2002/0156528 A1 | | 10/2002 | Gau | |
| 2003/0191534 A1 | * | 10/2003 | Viart et al. | 623/17.15 |
| 2003/0199982 A1 | * | 10/2003 | Bryan | 623/17.16 |
| 2004/0093082 A1 | * | 5/2004 | Ferree | 623/17.11 |

* cited by examiner

*Primary Examiner*—Corrine M McDermott
*Assistant Examiner*—Christopher D Prone
(74) *Attorney, Agent, or Firm*—Moser IP Law Group

(57) ABSTRACT

Provided is an implant comprising: a platform; a deformable pad affixed to the platform and adapted to seat two or more bearings; and the two or more bearings. The deformable pad can have a number of neutral positions matching the number of bearings, with the deformability of the pad adapted to apply force on the bearings any time the bearings are displaced laterally, with the force being in the direction of the corresponding neutral position.

17 Claims, 3 Drawing Sheets

DYNAMIC SPINAL IMPLANT OR JOINT REPLACEMENT

The present invention relates to an implant that can be used for replacing a spinal disk or a joint between two bones. The implant allows cushioned, dynamic motion of the adjoining vertebrae or bones.

Disc implants 1 are used to replace damaged spinal disks and provide the function of stabilizing the adjacent vertebrae 2 (see FIG. 1). The most traditional implants have provided a framework for bone growth that serves to fuse the adjacent vertebrae. There have been attempts to design implants that allow more dynamic, post-surgery movement, such as better accommodating the compression indicated by the arrows in FIG. 1. One attempt has used a deformable material sandwiched between two titanium platforms that fuses to the adjacent vertebrae. Other attempts use articulating pivot or ball socket type constructs. These articulating pivot or ball socket type constructs have not provided the dynamism necessary, due either to mechanical or construct failure or poor physiologic bone implant incorporation. Further efforts to make more dynamic implants are reviewed in "Lumbar Artificial Disc Surgery for Chronic Back Pain," by Jack Zigler, at http://www.spinehealth.com/research/discupdate/artificial/artificial01.html (recited as updated Mar. 15, 2004).

The current invention is believed to provide dynamic movement by allowing the construct components to integrate functionally into a coupled spine The spinal implant of the invention is designed to allow the transmission of physiologic stress at the bone-implant interface, while allowing for eventual rigid bone incorporation of the implant. A depressible pad allows for coupled movement with the spinal segments superiorly and inferiorly by allowing for complex motion in multiple planes. The depressible pad allows for dissipation of axial loads while a graded contoured FIG. 8 design allows for synchronization of movement across the midline with sagittal (midline) and rotational conformity. Symmetric design with graded eccentric contours allows for constrained and limited eccentric motion away from the midline.

SUMMARY OF THE INVENTION

In one embodiment, the invention provides an implant comprising: a platform; a deformable pad affixed to the platform and adapted to seat two or more bearings; and the two or more bearings. The deformable pad can have a number of neutral positions matching the number of bearings, with the deformability of the pad adapted to apply force on the bearings any time the bearings are displaced laterally, with the force being in the direction of the corresponding neutral position.

In another embodiment, the invention provides a method of replacing a spinal disk while providing rotation and flexing of adjacent vertebrae, the method comprising: placing between the vertebrae a bearing bed comprising a platform and a deformable pad affixed to the platform and adapted to seat two or more bearings, the placing made with the titanium platform seated against a first of the two vertebrae; and seating the two or more bearings in the bearing bed.

In a further embodiment, the invention provides a method of replacing a joint between two articulating bones comprising: placing between the bones a bearing bed comprising a platform and a deformable pad affixed to the platform and adapted to seat two or more bearings, the placing made with the platform seated against a first of the two bones; placing between the bones a second bearing bed comprising a platform and a deformable pad affixed to the platform and adapted to seat two or more bearings, the placing made with the platform seated against a second of the two bones; and seating the two or more bearings in the bearing bed such that the bearings rest in both bearing beds.

DETAILED DESCRIPTION OF THE INVENTION

Figure 1:
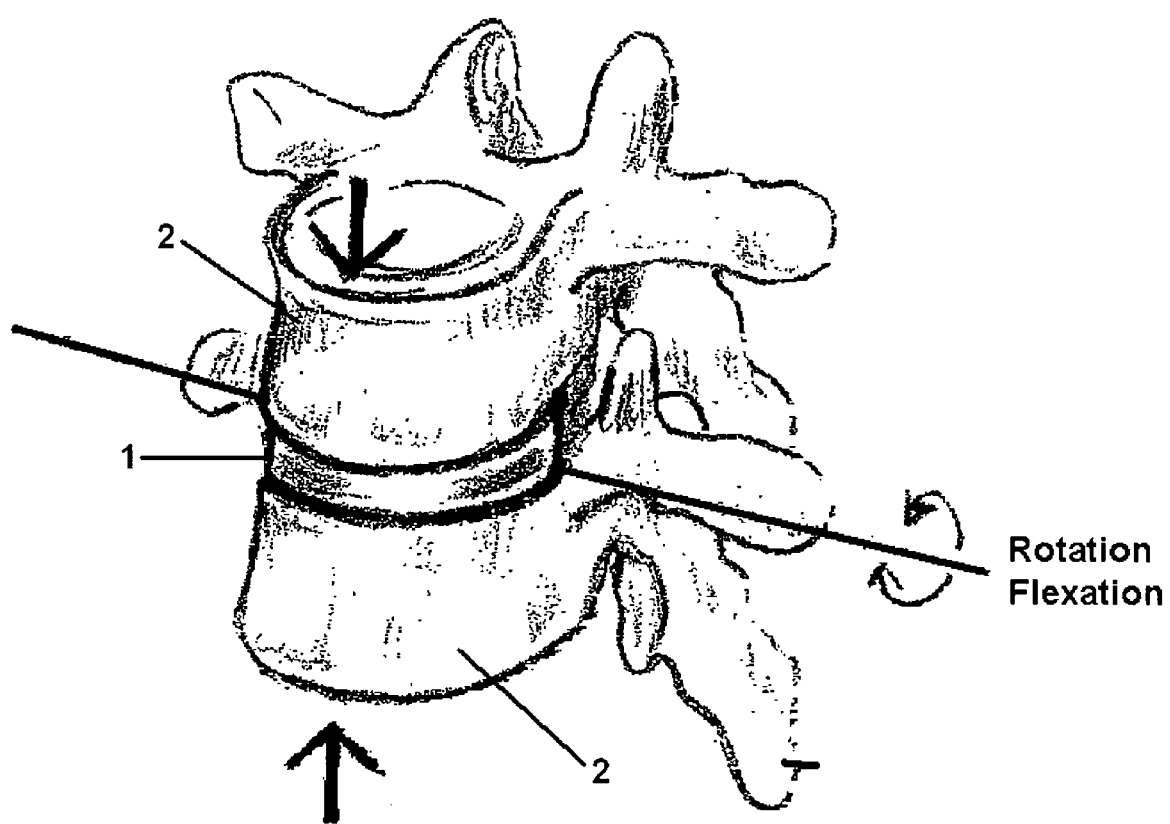
FIG. 1 displays two vertebrae with an artificial implant serving as the disk.
Figure 2A:
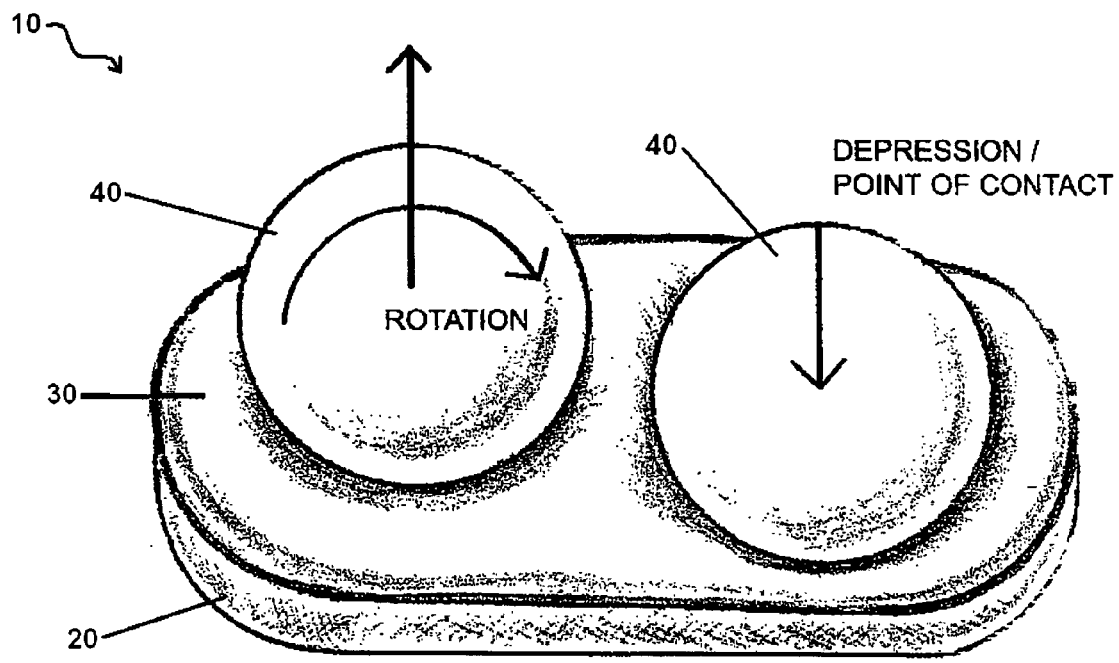
FIGS. 2A and 2B show a perspective and side view of an implant of the invention.
Figure 2B:
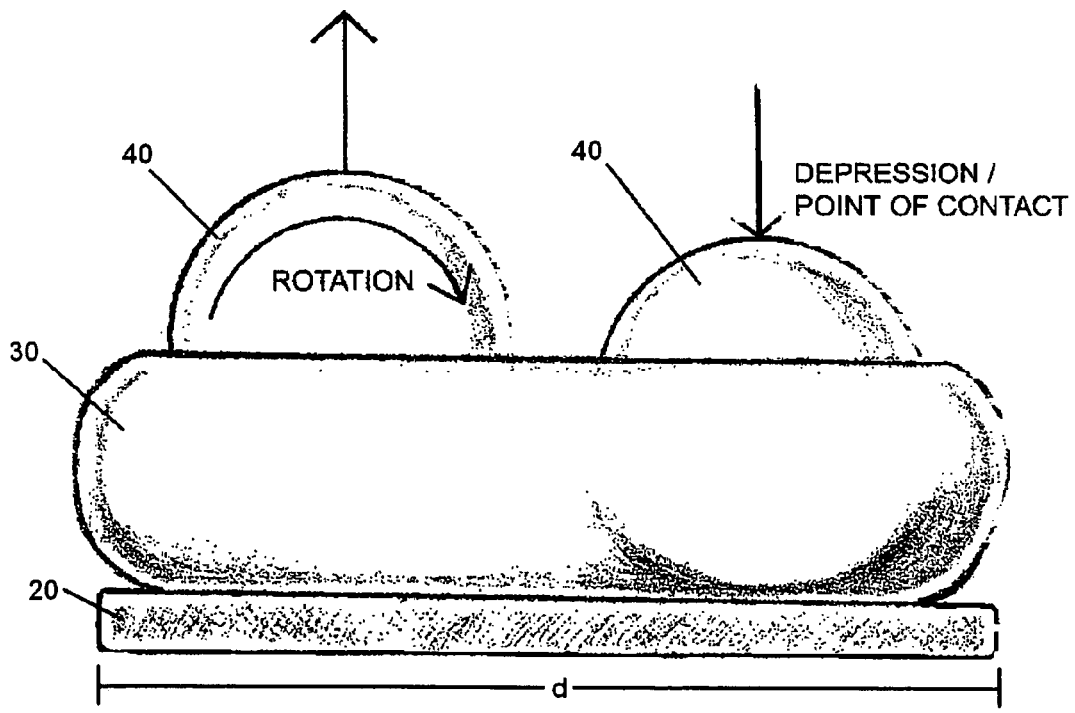

As shown with the exemplary embodiment of FIGS. 2A and 2B, provided is a platform 20, deformable pad 30 and, for example, two bearings 40, the combination providing implant 10. The platform is placed against a first vertebrae, and the bearings against a second vertebrae. Because the bearings can move within certain boundaries and can rotate, they allow the supported vertebrae to move relative to one another. The deformability of the deformable pad provides that the bearings will be pressed against and seated against the second vertebrae.

Figure 3:
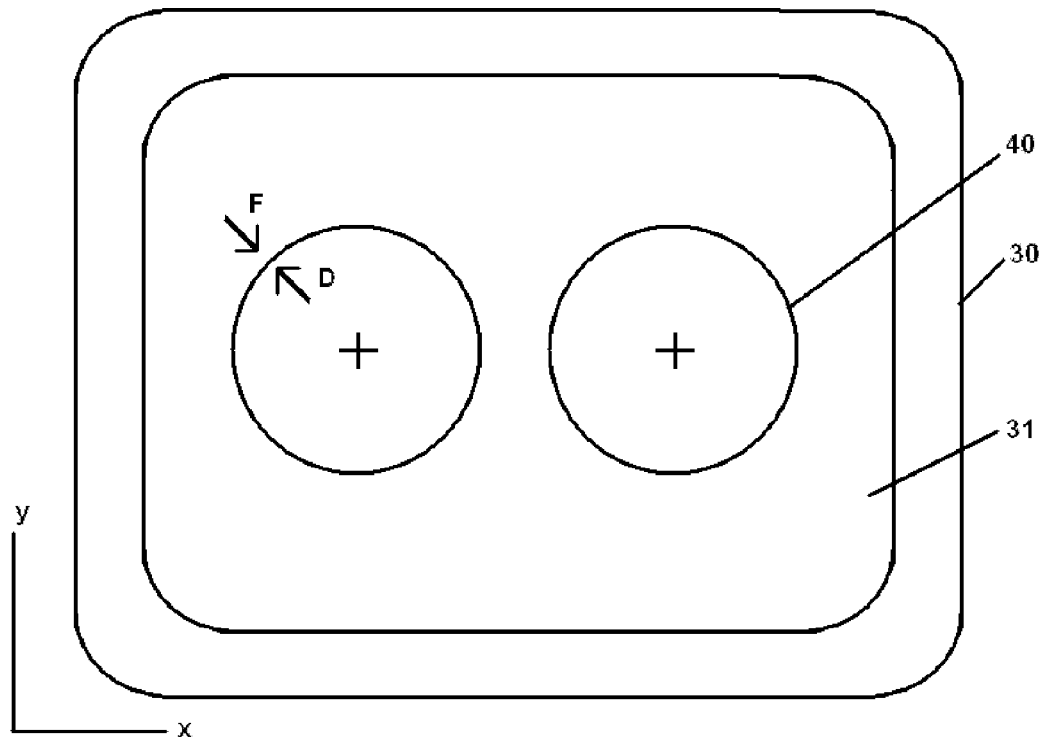
FIG. 3 shows a top view of the illustrative implant.

By use of a difference in compressibility in the deformable pad, optionally in combination with indentations in the deformable pad, the bearings are energy biased to a neutral position. The neutral positions are defined in an x-y axis as illustrated in FIG. 3, where the cross marks indicate the neutral positions. This is the position favored when the implant (when used as a spinal implant) is at the neutral axis. When forces on the implant displace the bearings away from the neutral position, the deformable pad is compressed so as to push the bearings towards their neutral position. Thus, as illustrated, displacement D generates a force F of a magnitude related to the size of the displacement. Of course, when force loaded in this way the bearings are typically offset from the neutral position, but nonetheless the pad provides force to bias towards the neutral position as forces shift. Where two bearings are used, the differential compressibility defines a FIG. 8 that bounds the movement of the bearings in the deformable pad. In FIG. 3, pad 30 has top surface 31.

In exemplary embodiment of FIG. 2, the bearings can be, for example, 9-15 mm in diameter, distance d can be, for example, 24-30 cm. In certain embodiments, the bearing diameter is from one of the following lower values to one of the following higer values, or between the values. The lower values are 9, 10, 11, 12, 13 or 14 mm. The higher values are 10, 11, 12, 13, 14 or 15 mm. The axis defining d is typically installed along the left lateral side to right lateral side axis of the patient. The depth of the device, anterior to posterior as placed in a patient, can be for example 18-24 cm. These dimensions will vary with, among other things, age, spinal level, or physiology.

The arrows in FIGS. 2A and 2B illustrate how the implant can dynamically accommodate side-to-side compression with complementary expansion. Thus, FIGS. 2A and 2B illustrate how coupled motion asymmetric load will cause the contralateral side to rise in the y-axis and rotate in the z-axis and translate in the x-axis as the ipsilateral side is depressed and loaded.

Figure 4:
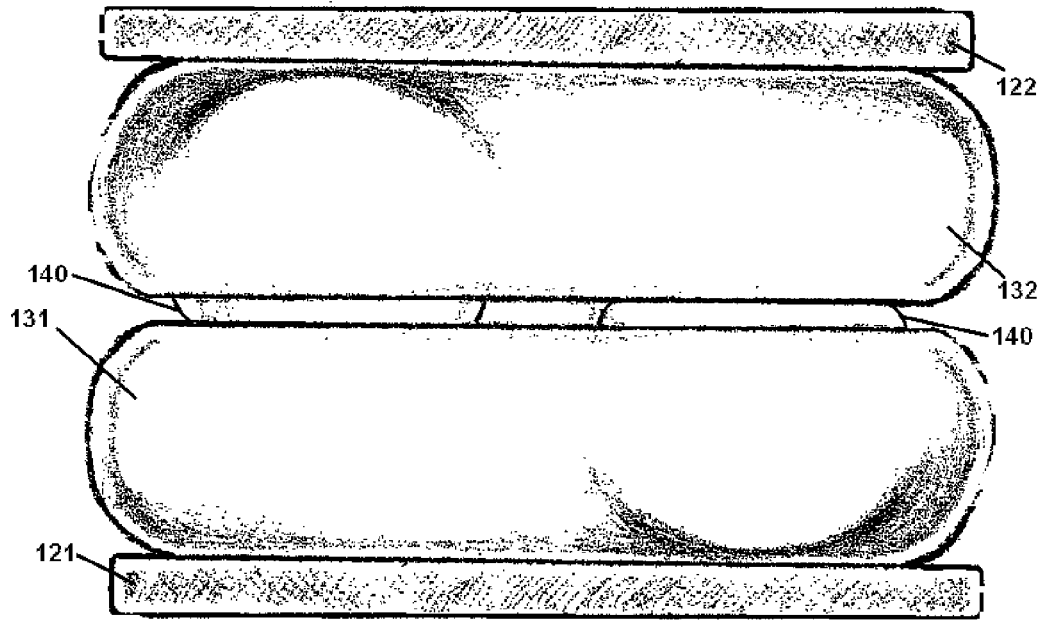
FIG. 4 shows an analogous sandwich structure for the implant.

In certain embodiments there is a second combination of deformable pad and platform placed on the other side of the bearings from the first. One can picture a mirror image of the first deformable pad and platform in FIG. 2A (though strict symmetry is not required). Hence, we have a sandwich structure of: first platform, first deformable pad, bearings, second deformable pad and second platform. This embodiment can be used for spinal implants, or to replace a joint between two articulating bones, such as a knee or elbow. For example, FIG. 4 shows a mirror image second deformable pad 132 and platform 122 placed, as described above, relative to the first deformable pad 131 and platform 121. The pads and platforms of FIG. 4 are arrayed as in FIG. 2A, or as the mirror image of the corresponding component of FIG. 2A. The dyanamicly mobile bearings 140 are illustrated in the same position as in FIG. 2A.

The platform is made of a material that promotes fusion to bone, for instance, as is known in the art, titanium, tantalum, carbon fiber or the like. It will be recognized that two or more materials can be joined to form the platform, with the bone fusion function provided by one or more of the materials and placed appropriately for promoting bone fusion. When used as a disc implant, the platform is typically placed against the lower of the two vertebrae.

The base of the platform can be textured to provide one or more of (i) reducing slipping along the bone or (ii) providing a framework for bone growth (which promotes fusion of the platform with the bone) or (iii) providing structures that can be impressed into the bone.

The deformable pad can be constructed of a suitable polymer. For example, the deformable pad can be constructed of ultra high molecular weight polyethylene (Spine, Inc., Raynham, Mass.), surgical polyurethane (Zimmer Spine, Minneapolis, Minn.) or the like. As needed, these polymers can be augmented with elastomeric polymers and monomers. The deformable pad can have varying compressibility C such that the value of C is highest at the preferred seating locations for the bearings. Lower compressibility away from this preferred seating acts, when a given bearing moves out of the preferred seating to create pressure pushing the bearing back to a more preferred location. While there can be some indentation or socket depth at the preferred seating location, such depth preferably does not diminish the action of the deformable and resilient pad to push on the bearings and keep them snugly placed against the second vertebrae (or, in some embodiments, a second deformable pad).

A gradient of compressibility can be produced, for example, with a three-dimensional polymer printer. Those of skill will recognize how to vary compressibility in an elastomeric polymer with variation in crosslinker, elastomeric monomer, filler or the like. The printing can be of monomers or incomplete polymers, with the final polymer cured after the three-dimensional printing. Or, a stepwise gradient can be constructed by forming a first portion of the pad with least compressible polymer with a insert void, and filling the void with successive inserts of increasing compressibility (analogous to the inserts of nesting dolls). The inserts can be annealed with a compatible monomer mix. Or, an insert void can be cut from the first cured product having the least compressible polymer, and the void filled with a next successive compressible polymer. The process of making and filling voids can be repeated to provide the gradient in compressibility.

The bearings are sized and provided in a number such that, from the combination, the second vertebrae is appropriately supported. Where two bearings are used, the bearings will typically be somewhat larger than is needed with three or more bearings. It will be recognized that over time, the bone at the second vertebrae will reshape somewhat consistent with the shape and movement of the bearings. The bearings resist adhering to the second vertebrae due to shape and movement, but can also be constructed of a material selected to resist such adherence. The bearings can be made, for example, of a suitable composite, titanium, or other material suitable for use in a rotatable internal prosthesis.

DEFINITIONS

The following terms shall have, for the purposes of this application, the respective meanings set forth below.

Laterally Offset

The spine of a patient has an anterior side, right lateral side (from the perspective of the patient), a posterior side, and a left lateral side. Bearings are "laterally offset" if two or more are such that their centers of mass would be on opposite sides of a hypothetical anterior to posterior line bisecting at the midpoint of the spine, with 25% or less of any of these two bearings overlaps the hypothetical line.

Publications and references, including but not limited to patents and patent applications, cited in this specification are herein incorporated by reference in their entirety in the entire portion cited as if each individual publication or reference were specifically and individually indicated to be incorporated by reference herein as being fully set forth. Any patent application to which this application claims priority is also incorporated by reference herein in the manner described above for publications and references.

While this invention has been described with an emphasis upon preferred embodiments, it will be obvious to those of ordinary skill in the art that variations in the preferred devices and methods may be used and that it is intended that the invention may be practiced otherwise than as specifically described herein. Accordingly, this invention includes all modifications encompassed within the spirit and scope of the invention as defined by the claims that follow.

What is claimed:

1. An implant comprising:
    a platform having two major surfaces, a first major surface adapted to seat against a vertebrae in place of a vertebral disk, and a second major surface;
    a deformable pad having two major surfaces, a first pad major surface affixed to the second platform major surface and a second major pad surface adapted to seat two or more round bearings such that the bearings can rotate; and
    the two or more round bearings which are rotatable as seated on the pad.

2. The implant of claim 1, wherein the deformable pad has a number of neutral positions matching the number of bearings, the deformability of the pad adapted to apply force on the bearings when the bearings are displaced laterally from the neutral position, with the force being in the direction of the corresponding neutral position.

3. The implant of claim 1, wherein the deformable pad has varying compressibility C such that the value of C is highest at the preferred seating locations for the bearings, and decreases with displacement away from such preferred seating locations in an amount effective to promote, when the implant is in use, returning the bearings to preferred seating locations when displacing stresses are removed.

4. The implant of claim 1, adapted to provide an artificial joint, further comprising:
    a second said platform; and
    a second said deformable pad affixed to the second platform and adapted to seat the two or more round rotatable bearings, wherein the first platform is adapted to sit on one side of the bearings, and the second platform is adapted to sit on the other side.

5. The implant of claim 1, adapted to provide an artificial joint, consisting essentially of:
   (A) the platform, the deformable pad, and the two or more round rotatable bearings; and
   (B) a second said platform, and a second said deformable pad affixed to the second platform and adapted to seat the two or more round rotatable bearings, wherein the first platform is adapted to sit on one side of the bearings, and the second platform is adapted to sit on the other side.

6. A method of replacing a spinal disk while providing rotation and flexing of adjacent vertebrae, the method comprising:
   providing the implant of claim 1;
   placing between the vertebrae the bearing bed comprising the platform and the deformable pad affixed to the platform and adapted to seat two or more bearings, the placing made with a titanium platform seated against a first of the two vertebrae; and
   seating the two or more bearings in the bearing bed.

7. The method of claim 6, wherein the seating is such that the bearings rest against the second of the two vertebrae.

8. The method of claim 7, wherein in the placing step cleats on the platform are seated against the first of the two vertebrae.

9. The method of claim 7, wherein in the placing step the bearings are seated so that they are laterally offset.

10. The method of claim 6, comprising in the placing step using a bearing bed wherein the deformable pad has a number of neutral positions matching the number of bearings, the deformability of the pad adapted to apply force on the bearings any time the bearings are displaced laterally, with the force being in the direction of the corresponding neutral position.

11. A method of replacing a joint between two articulating bones comprising:
   providing the implant of claim 1;
   placing between the bones the bearing bed comprising the platform and the deformable pad affixed to the platform and adapted to seat two or more bearings, the placing made with the platform seated against a first of the two bones;
   placing between the bones a second bearing bed comprising a platform and a deformable pad affixed to the platform and adapted to seat two or more bearings, the placing made with the platform seated against a second of the two bones; and
   seating the two or more bearings in the bearing bed such that the bearings rest in both bearing beds.

12. The method of claim 11, wherein in the first placing step cleats on the first platform are seated against the first of the two bones.

13. The method of claim 11, wherein in the placing step the bearings are seated so that they are laterally offset.

14. The method of claim 11, comprising in the placing steps using bearing beds wherein the deformable pad has a number of neutral positions matching the number of bearings, the deformability of the pad adapted to apply force on the bearings any time the bearings are displaced laterally, with the force being in the direction of the corresponding neutral position.

15. An implant consisting essentially of:
   a platform having two major surfaces, a first major surface adapted to seat against a vertebrae in place of a vertebral disk, and a second major surface;
   a deformable pad having two major surfaces, a first pad major surface affixed to the second platform major surface and a second major pad surface adapted to seat two or more round bearings such that the bearing can rotate; and
   the two or more round bearings which are rotatable as seated on the pad.

16. The implant of claim 15, wherein the deformable pad has a number of neutral positions matching the number of bearings, the deformability of the pad adapted to apply force on the bearings any time the bearings are displaced laterally from the neutral position, with the force being in the direction of the corresponding neutral position.

17. The implant of claim 15, wherein the deformable pad has varying compressibility C such that the value of C is highest at the preferred seating locations for the bearings, and decreases with displacement away from such preferred seating locations in an amount effective to promote, when the implant is in use, returning the bearings to preferred seating locations when displacing stresses are removed.

* * * * *